(12) United States Patent
Grady et al.

(10) Patent No.: US 8,965,077 B2
(45) Date of Patent: Feb. 24, 2015

(54) METHODS AND SYSTEMS FOR FAST AUTOMATIC BRAIN MATCHING VIA SPECTRAL CORRESPONDENCE

(75) Inventors: Leo Grady, Yardley, PA (US); Herve Jun Alfred Lombaert, Montreal (CA); Jonathan Rizzo Polimeni, Cambridge, MA (US); Farida Cheriet, Montreal (CA)

(73) Assignees: Siemens Corporation, Iselin, NJ (US); The General Hospital Corporation, Boston, MA (US)

( * ) Notice: Subject to any disclaimer, the term of this patent is extended or adjusted under 35 U.S.C. 154(b) by 957 days.

(21) Appl. No.: 13/107,002

(22) Filed: May 13, 2011

(65) Prior Publication Data

US 2011/0295515 A1    Dec. 1, 2011

Related U.S. Application Data

(60) Provisional application No. 61/345,714, filed on May 18, 2010.

(51) Int. Cl.
*G06K 9/00* (2006.01)
*A61B 5/00* (2006.01)
(Continued)

(52) U.S. Cl.
CPC ............ *A61B 5/4064* (2013.01); *G06T 7/0028* (2013.01); *A61B 5/055* (2013.01); *A61B 5/72* (2013.01); *A61B 2576/026* (2013.01); *G06T 2200/04* (2013.01); *G06T 2207/10088* (2013.01); *G06T 2207/20072* (2013.01); *G06T 2207/30016* (2013.01)
USPC ........... 382/128; 382/130; 382/131; 382/132; 702/19; 702/189

(58) Field of Classification Search
CPC ............ A61B 2576/026; A61B 5/055; A61B 5/4064; A61B 5/72; G06K 9/00
USPC ......... 382/128, 129, 130, 131, 132, 255, 159; 702/19, 189; 706/52
See application file for complete search history.

(56) References Cited

U.S. PATENT DOCUMENTS

2004/0194051 A1* 9/2004 Croft ............................... 716/20
2010/0111370 A1* 5/2010 Black et al. ................... 382/111
2013/0163837 A1* 6/2013 Zabair et al. .................. 382/128

OTHER PUBLICATIONS

Q. Anqi, D. Bitouk, and M.I. Miller. Smooth functional and structural maps on the neocortex via orthonormal bases of the Laplace-Beltrami operator. Trans. Med. Im., 25(10), 2006.

(Continued)

*Primary Examiner* — Ali Bayat (57) ABSTRACT

Methods and systems determine a correspondence of two sets of data, each data set represents an object. A weighted graph is created from each data set, and a Laplacian is determined for each weighted graph, from which spectral components are determined. The spectral components determine a coordinate of a node in a weighted graph. Nodes of a weighted graph are weighted with a quantified feature related to anode. A coordinate related to a quantified feature of a node is added to the coordinate based on the spectral components. Spectral components related to a weighted graph are reordered to a common ordering. Reordered spectral components related to the first and second data set are aligned and a correspondence is determined. An object may be a brain and a feature may be a sulcal depth. Other objects for which a correspondence may be determined include an electrical network, an image and a social network.

12 Claims, 7 Drawing Sheets

(51) Int. Cl.
*G06T 7/00* (2006.01)
*A61B 5/055* (2006.01)

(56) References Cited

OTHER PUBLICATIONS

B. Fischl, N. Rajendran, E. Busa, J. Augustinack, O. Hinds, B. T. Thomas Yeo, H. Mohlberg, K. Amunts, and K. Zilles. Cortical folding patterns and predicting cytoarchitecture. Cereb Cortex, 18(8), 2007.
B. Fischl, M. I. Sereno, R. B. Tootell, and A. M. Dale. High-resolution intersubject averaging and a coordinate system for the cortical surface. Human Brain Mapping, 8(4), 1999.
B. Fischl, A. van der Kouwe, C. Destrieux, E. Halgren, F. Segonne, D. H. Salat, E. Busa, L. J. Seidman, J. Goldstein, D. Kennedy, V. Caviness, N. Makris, B. Rosen, and A. M. Dale. Automatically parcellating the human cerebral cortex. Cereb. Cortex, 14(1), 2004.
O. P. Hinds, N. Rajendran, J. R. Polimeni, J. C. Augustinack, G. Wiggins, L. L. Wald, Diana H. Rosas, A. Potthast, E. L. Schwartz, and B. Fischl. Accurate prediction of V1 location from cortical folds in a surface coordinate system. NeuroImage, 39(4), 2008.
V. Jain and H. Zhang. Robust 3D shape correspondence in the spectral domain. In Int. Conf. on Shape Mod. and App., 2006.
G. Lohmann, D. Y. von Cramon, and A. C. Colchester. Deep sulcal landmarks provide an organizing framework for human cortical folding. Cereb Cortex, 18(6), 2008.
D. Mateus, R. Horaud, D. Knossow, F. Cuzzolin, and E. Boyer. Articulated shape matching using Laplacian eigenfunctions and unsupervised point registration. In CVPR, 2008.
A. Myronenko and X. Song. Point-set registration: Coherent point drift. PAMI, 2009.
M. Niethammer, M. Reuter, F. E. Wolter, S. Bouix, N. Peinecke, M. S. Koo, and M. Shenton. Global Medical Shape Analysis Using the Laplace-Beltrami Spectrum. In MICCAI, 2007.
M. Reuter. Hierarchical shape segmentation and registration via topological features of Laplace-Beltrami eigenfunctions. Int. Journal Comp. Vis., 2009.
M. Reuter, F. E. Wolter, M. Shenton, and M. Niethammer. Laplace-Beltrami eigenvalues and topological features of eigenfunctions for statistical shape analysis. Comput. Aided Des., 41(10), 2009.
P. Thompson and A. W. Toga. A surface-based technique for warping three-dimensional images of the brain. Trans. on Med. Im., 15(4), 1996.
S. Umeyama. An eigendecomposition approach to weighted graph matching problems. PAMI, 10(5), 1988.
D. C. Van Essen and H. A. Drury. Structural and functional analyses of human cerebral cortex using a surface-based atlas. J. Neurosci., 17(18), 1997.
Y. Zheng and D. Doermann. Robust point matching for nonrigid shapes by preserving local neighborhood structures. PAMI, 28(4), Apr. 2006.

* cited by examiner

METHODS AND SYSTEMS FOR FAST AUTOMATIC BRAIN MATCHING VIA SPECTRAL CORRESPONDENCE

CROSS-REFERENCE TO RELATED APPLICATIONS

This application claims the benefit of U.S. Provisional Application No. 61/345,714, filed May 18, 2010, which is incorporated herein by reference.

BACKGROUND OF THE INVENTION

The present invention relates to methods and systems for automatic brain matching. More specifically, it is related to automatic matching of brain images using spectral correspondence.

Brain matching is an important problem in neuroimaging studies. Current surface-based methods for cortex matching and atlasing, although quite accurate, can require long computation times. Accordingly, novel and improved methods and systems for brain matching are required.

SUMMARY OF THE INVENTION

One aspect of the present invention presents a novel method and system that will provide a matching of two objects based on spectral matching. As an aspect of the present invention matching methods and systems based on spectral correspondence are provided, where spectra of graphs derived from the surface model meshes are matched. Cerebral cortex matching problems can thus benefit from the tremendous speed advantage of spectral methods, which are able to calculate a cortex matching in seconds rather than hours. Moreover, spectral methods are extended in order to use additional information that can improve matching. Additional information, such as sulcal depth, surface curvature, and cortical thickness can be represented in a flexible way into graph node weights (rather than only into graph edge weights) and as extra embedded coordinates.

In accordance with an aspect of the present invention, a method for determining a correspondence between a first and a second set of data elements representing a first and a second object, respectively, is described and claimed. A processor processes the first and second set of data elements to be represented as a first and second weighted graph, respectively, and a weight is provided to an edge of the first and second weighted graphs to generate a first and a second Laplacian matrix. The processor determines a first and a second plurality of eigenvectors of the first and second Laplacian matrix. The processor assigns a coordinate to each node in the first and second weighted graph, wherein the coordinate is based on a spectral component related to the weighted graph of the node. The processor also assigns an additional coordinate to each node in the first and second weighted graph, wherein the additional coordinate is based on a quantified feature of the object. The processor reorders the first and second plurality of eigenvectors of the first and second spectrum to generate a reordered first spectrum and a reordered second spectrum and the processor aligns the first reordered spectrum and the second reordered spectrum to determine a correspondence between the first and second set of data using eigenvector information related to the first and the second plurality of eigenvectors.

The first and second Laplacian matrix each reflects a weight of a node in a related weighted graph. The weight of the node can be based on a quantified feature of the node. The reordering can be applied to create a common ordering of the eigenvectors. The aligning of the first reordered spectrum and the second reordered spectrum can be performed using the coordinates of the nodes.

In accordance with an aspect of the present invention, the first object is a brain and the quantified feature is a sulcal depth. In accordance with another aspect of the present invention, the first object is an electrical network. It can also be a social network.

In accordance with a further aspect of the present invention, a method for determining a correspondence between a first set of data and a second set of data, representing a first brain and a second brain, respectively, is provided. A processor creates a first mesh from the first set of data and a second mesh from the second set of data, determines a Laplacian matrix for a weighted graph representing a mesh, determines by eigendecomposition a first and a second spectrum related to the first and second mesh, assigns to each node in each mesh a coordinate based on a spectral component of the related spectrum, assigns to each node in each mesh an additional coordinate based on a quantified feature of the node, reorders the first and second spectrum to create a common ordering of eigenvectors and aligns the reordered first and second spectrum, Then the processor determines a correspondence between the first and second mesh by matching spectral component based coordinates of nodes in the first and the second mesh.

The Laplacian matrix reflects a weight of a node in its related weighted graph that expresses a quantified feature of the node. The quantified feature of the additional coordinate can be selected from the group consisting of a sulcal depth, a brain curvature and a cortical thickness. It can also be selected from the group consisting of a sulcal depth, a brain curvature and a cortical thickness.

Another aspect of the present invention contemplates a system to determine a correspondence between a first set of data and a second set of data, representing a first brain and a second brain, respectively. The system includes a memory, enabled to store the first set of data, the second set of data and instructions. It also includes a processor, enabled to retrieve instructions from the memory to any of the above steps or any other step described herein.

DESCRIPTION OF A PREFERRED EMBODIMENT

The human cerebral cortex is composed of many distinct brain areas whose locations relative to the folding pattern are highly stereotyped. In many neuroimaging studies, finding corresponding locations between two individuals allows data to be pooled across subjects and enables the investigation of functional and anatomical differences between individuals. Early attempts at computing correspondences relied on the extrinsic geometry seen on brain volumetric images. In 1967, "J. Talairach, G. Szikla, P. Tournoux, A. Prosalentis, M. Bordas-Ferrier, L. Covello, M. Iacob, and E. Mempel. Atlas d'anatomie stereotaxique du telencephale. Masson, Paris, 1967" introduced an early version of a brain atlas in the form of a 3D stereotaxic coordinate system.

Despite its popularity, this method matched volumetric brain data using 3D Euclidean distances, which ignored geometric variabilities in the folding pattern. Techniques based on high-dimensional deformations allow for the alignment of volumetric brain image data. However, the lack of an explicit model for the brain surface often creates misaligned cortical areas as described in "K. Amunts, A. Malikovic, H. Mohlberg, T. Schormann, and K. Zilles. Brodmann's areas 17 and 18 brought into stereotaxic space-where and how variable? NeuroImage, 11(1), 2000."

Later, it was demonstrated that surface-based alignment as described in "B. Fischl, M. I. Sereno, R. B. Tootell, and A. M. Dale. High-resolution intersubject averaging and a coordinate system for the cortical surface. Human Brain Mapping, 8(4), 1999", "B. Fischl, N. Rajendran, E. Busa, J. Augustinack, O. Hinds, B. T. Thomas Yeo, H. Mohlberg, K. Amunts, and K. Zilles. Cortical folding patterns and predicting cytoarchitecture. Cereb Cortex, 18(8), 2007", "H. A. Drury, D. C. Van Essen, S. C. Joshi, and M. I. Miller. Analysis and comparison of areal partitioning schemes using 2-D uid deformations. NeuroImage, 3, 1996", "D. C. Van Essen and H. A. Drury. Structural and functional analyses of human cerebral cortex using a surface-based atlas. J. Neurosci., 17(18), 1997" and "P. Thompson and A. W. Toga. A surface-based technique for warping three-dimensional images of the brain. Trans. on Med. Im., 15(4), 1996", which operates by directly registering surface models of the cerebral cortex, significantly outperforms volume-based approaches as described in "B. Fischl, M. I. Sereno, R. B. Tootell, and A. M. Dale. High-resolution intersubject averaging and a coordinate system for the cortical surface. Human Brain Mapping, 8(4), 1999" and "B. Fischl, N. Rajendran, E. Busa, J. Augustinack, O. Hinds, B. T. Thomas Yeo, H. Mohlberg, K. Amunts, and K. Zilles. Cortical folding patterns and predicting cytoarchitecture. Cereb Cortex, 18(8), 2007."

The success of these surface-based techniques depends on the stability of the folding pattern across subjects. Some cortical areas are indeed consistently in a fixed position relative to the folding pattern as described in "B. Fischl, M. I. Sereno, R. B. Tootell, and A. M. Dale. High-resolution intersubject averaging and a coordinate system for the cortical surface. Human Brain Mapping, 8(4), 1999" and "G. Lohmann, D. Y. von Cramon, and A. C. Colchester. Deep sulcal landmarks provide an organizing framework for human cortical folding. Cereb Cortex, 18(6), 2008," whereas other areas float around and do not seem well correlated to the folding pattern. These areas, however, may be correlated with measurable anatomical features other than the explicit cortical geometry.

One successful method for computing brain surface correspondences was introduced by Fischl et al. in "B. Fischl, M. I. Sereno, R. B. Tootell, and A. M. Dale. High-resolution intersubject averaging and a coordinate system for the cortical surface. Human Brain Mapping, 8(4), 1999." It inflates each cerebral hemisphere surface to a sphere by a process that minimizes metric distortions, thus preserving local distances and areas. The cortical surface model is then mapped to the sphere using a nonrigid deformation driven by geometric features of the original folding pattern.

This is the method used by FreeSurfer, a leading and widely used tool for brain surface reconstruction, matching, and atlasing. Despite its accuracy, FreeSurfer suffers from a severe computational burden, which causes it to be very slow. It can take hours to compute a correspondence map between two cerebral cortices.

In order to alleviate this severe computational burden, a different approach for brain surface matching is provided herein as an aspect of the present invention, based on spectral correspondence. Spectral methods as described in "F. Chung. Spectral Graph Theory (CBMS Conf. in Math., No. 92). AMS, 1997" present the tremendous advantage of being extremely fast, on the order of seconds. Correspondences are found on a graph spectrum, which is essentially the eigendecomposition of the graph Laplacian of an underlying shape model as for instance illustrated in FIG. 1.

Figure 1:
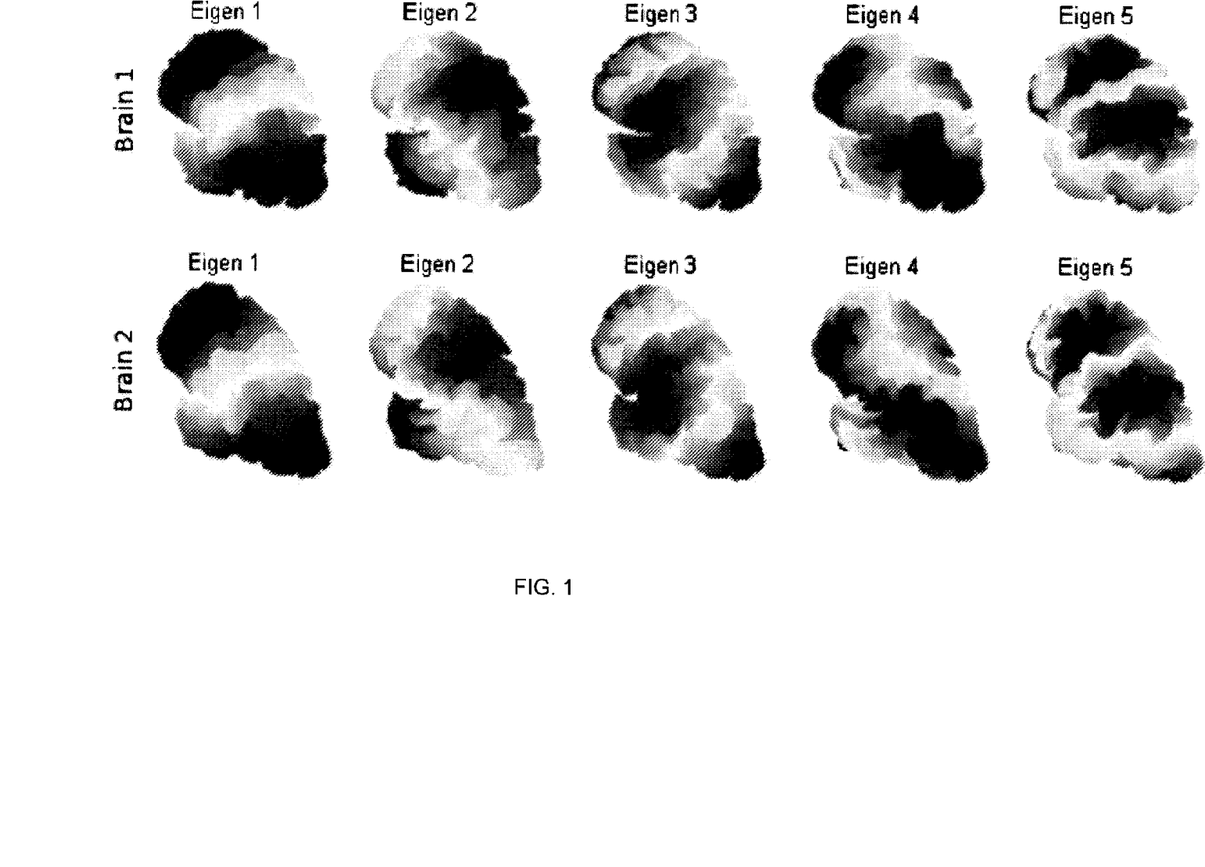
FIG. 1 illustrates a eigendecomposition of a graph Laplacian.

FIG. 1 illustrates the eigendecomposition of the graph Laplacian (using equation (2) which is provided later herein) showing the first six eigenvectors (or six spectral components, one per column) of two brain surfaces (top and bottom rows). The grey level indicates a spectral coordinate for each point.

Spectral methods have already been used in many fields, including in computer vision with the segmentation and registration of shapes in images as described in "M. Reuter. Hierarchical shape segmentation and registration via topological features of Laplace-Beltrami eigenfunctions. Int. Journal Comp. Vis., 2009" and recently in medical applications with the analysis of brain shape features as described in "M. Niethammer, M. Reuter, F. E. Wolter, S. Bouix, N. Peinecke, M. S. Koo, and M. Shenton. Global Medical Shape Analysis Using the Laplace-Beltrami Spectrum. In MICCAI, 2007" and "M. Reuter, F. E. Wolter, M. Shenton, and M. Niethammer. Laplace-Beltrami eigenvalues and topological features of eigenfunctions for statistical shape analysis. Comput. Aided Des., 41(10), 2009" and with the smoothing of cortical surfaces as described in "Q. Anqi, D. Bitouk, and M. I. Miller. Smooth functional and structural maps on the neocortex via orthonormal bases of the Laplace-Beltrami operator. Trans. Med. Im., 25(10), 2006.

Umeyama in "S. Umeyama. An eigendecomposition approach to weighted graph matching problems. PAMI, 10(5), 1988" and later Scott and Longuet-Higgins in "G. L. Scott and H. C. Longuet-Higgins. An algorithm for associating the features of two images. Proc Bio. Sc., 244(1309), 1991" pioneered the use of spectral methods for the correspondence problem. Shapiro and Brady in "L. S. Shapiro and J. M. Brady. Feature-based correspondence: an eigenvector approach. Image Vis. Comp., 10(5), 1992" compared ordered eigenvectors of a proximity matrix to find correspondences. Their work served as a basis for future spectral correspondence methods. Variants include the use of different proximity matrices using different kernels, the use of the adjacency matrix, or different normalized Laplacian matrices. Mateus et al. in "D. Mateus, R. Horaud, D. Knossow, F. Cuzzolin, and E. Boyer. Articulated shape matching using Laplacian eigenfunctions and unsupervised point registration. In CVPR, 2008" proposed an original unsupervised spectral method with an alternative to eigenvalue ordering based on eigenvectors histograms and refining the eigenvectors alignment with a probabilistic point matching. Jain and Zhang in "Robust 3D shape correspondence in the spectral domain. In Int. Conf. on Shape Mod. and App., 2006" tackle the eigenvectors alignment with a nonrigid deformation based on thin plate splines.

Previous spectral correspondence methods employ solely geometric information by weighting the graph edges with the distances between connected pairs of vertices. However, in order to use certain quantities (like sulcal depth, surface curvature, or cortical thickness), the spectral correspondence approach is modified in accordance with an aspect of the present invention to incorporate information beyond edge length.

In accordance with an aspect of the present invention a structure or an object such as a brain is represented by a set of data elements which can be represented by a graph. Each data element or node in a graph can be provided with a feature defined by a relationship with nodes such as adjacent nodes and wherein such features are quantified. It is believed that aspects of the present invention that use node weighting in a spectral correspondence method are novel.

Some of the features (like curvature) can be determined purely from the mesh (as in the manner described). Other features (such as cortical thickness) are determined from an underlying MRI scan. All these methods of determining a feature are known and are published methods, for instance embodied in free public software (such as FreeSurfer), to extract these features. In other applications, these features might be determined purely from the graph structure or they might be provided via outside information. These features are in one aspect a basis of incorporating outside information.

Additional information will be incorporated into the Laplace operator, which implicitly contains metric information about nodes and edges. Moreover, additional information can be used as extra embedded coordinates when aligning the eigenvectors. This added level of flexibility makes the herein provided methods as an aspect of the present invention good candidates for brain studies involving various types of information with a large number of subjects.

After detailing the herein provided approach in the next section, it will be shown in a control experiment that additional information can dramatically improve the performance of a spectral method. Using data from 12 subjects, the herein provided method is validated by comparing the computed correspondences with those generated by FreeSurfer as described in "B. Fischl, M. I. Sereno, R. B. Tootell, and A. M. Dale. High-resolution intersubject averaging and a coordinate system for the cortical surface. Human Brain Mapping, 8(4), 1999." It will be demonstrated that the method provided herein produces results in a fraction of time required by FreeSurfer, and that the herein provided method approaches the accuracy of FreeSurfer. It is believed that this large gain in processing speed opens the door to new brain studies that were previously limited by the computational burden of the cortex matching calculation. Therefore, the herein provided method has the potential to be a significant tool for use in neuroscience and in other fields.

Method

The herein provided method finds correspondences by comparing cortex representations, called spectra (illustrated in for instance FIG. 1). The spectrum of a brain surface mesh is independent of its extrinsic geometry. In order to adapt a spectral method to brain surface matching, several issues must be solved. First, it will be shown below how additional information (such as sulcal depth as described in "B. Fischl, M. I. Sereno, R. B. Tootell, and A. M. Dale. High-resolution intersubject averaging and a coordinate system for the cortical surface. Human Brain Mapping, 8(4), 1999", surface curvature, and cortical thickness) can be used in spectral methods as weightings of the graph nodes. Second, the ordering of the spectral components is improved by finding an optimal permutation of the underlying eigenvectors. And third, the spectra are aligned in a multidimensional space using a non-rigid point transformation method. Steps of the method provided in accordance with an aspect of the present invention are summarized in FIG. 2.

Method Summary

Figure 2:
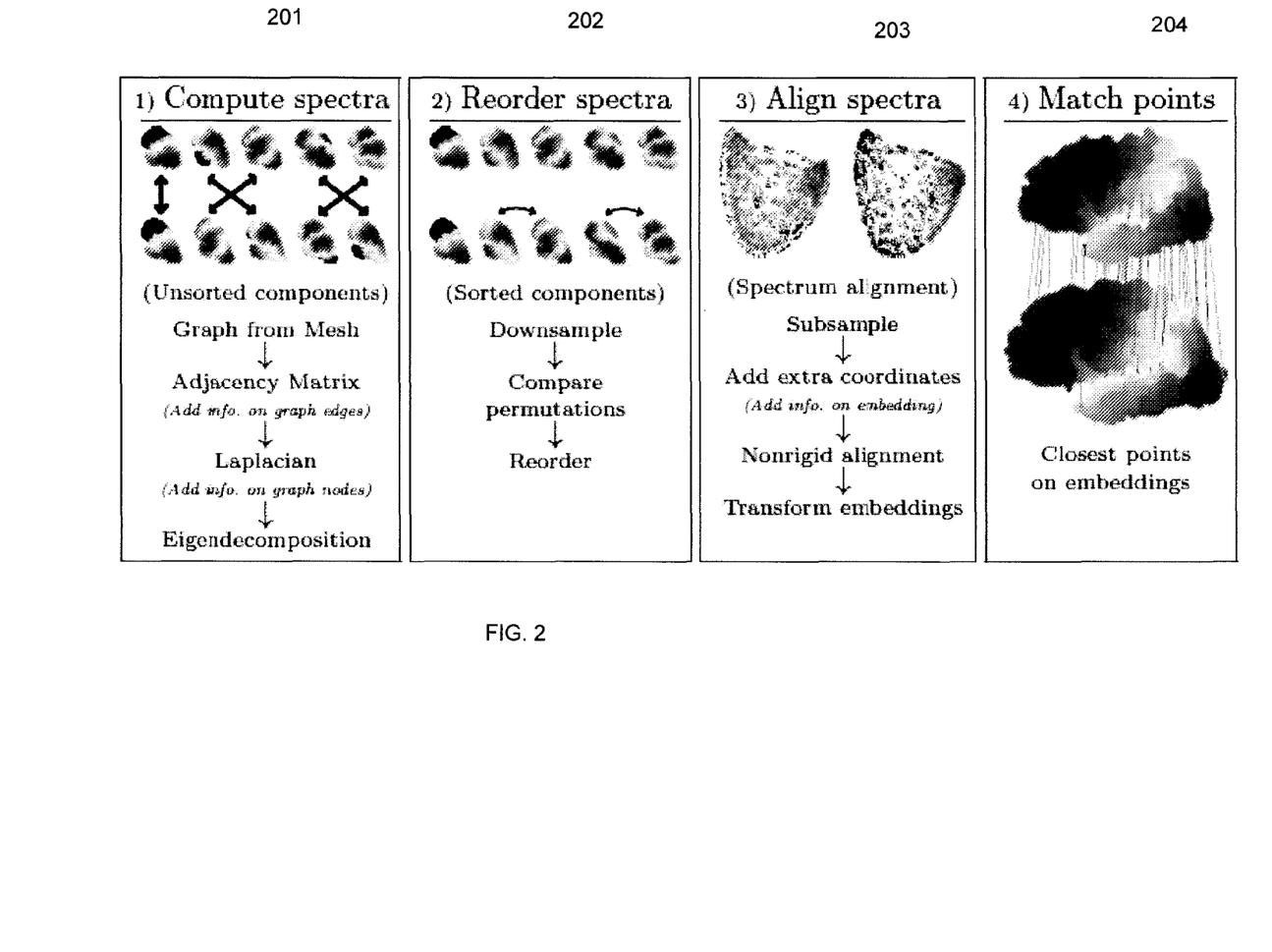
FIG. 2 illustrates steps in accordance with an aspect of the present invention.

Steps of the method as provided in accordance with an aspect of the present invention and illustrated in FIG. 2 are:
First, building two graphs and set the graph edges (the adjacency matrix) and the graph nodes (the Laplacian matrix). The eigendecomposition of the graph's Laplacian reveals the spectral components. (see panel 201 in FIG. 2)
Second, reordering the components by finding the optimal permutation of components. (see panel 202 in FIG. 2)
Third, deforming the spectral embeddings. (see panel 203 in FIG. 2)
Finally, matching points are found with closest points in both spectral representations. (see panel 204 in FIG. 2)

2.1 Spectral Correspondence

Given a shape defined by its collection of nodes $X=\{x_1, x_2, \ldots, x_n\}$ and a neighborhood system N connecting a subset of these nodes (e.g., a mesh with vertices and faces), it is possible to construct its corresponding graph $G_X$. Here, the adjacency matrix W is defined in terms of affinity weights as described in "L. Grady and J. R. Polimeni. Discrete Calculus: Applied Analysis on Graphs for Computational Science. Springer, 2010", which are derived from a distance metric $dist(x_i, x_j)$ between two neighboring vertices $(x_i, x_j)$ ($\epsilon$ is a small penalizing term):

$$W_{ij} = \begin{cases} (\text{dist}(i, j) + \varepsilon)^{-1}, & \text{if } i \in N(j), \text{ and } i \neq j \\ 0, & \text{otherwise} \end{cases} \quad (1)$$

It was shown in "L. Grady and J. R. Polimeni. Discrete Calculus: Applied Analysis on Graphs for Computational Science. Springer, 2010", that the general Laplacian operator on a graph takes the form $\tilde{L}=GL=G(D-W)$, where D is a diagonal matrix defined as $D_{ii}=\Sigma_j W_{ij}$ and G is the diagonal matrix of node weights. Typically in spectral correspondence, G is set to $G=D^{-1}$. However, herein as an aspect of the present invention it is provided to replace the default assignment $G=D^{-1}$ with any meaningful node weighting. Therefore, data associated with a mesh, such as distances or other additional information, can be incorporated in a graph on either its edges (in equation (1)), or its nodes by manipulating G.

It is assumed in accordance with an aspect of the present invention that the sulcal depth at each point, $\{s_1, s_2, \ldots, s_n\}$, the Gaussian curvature at each point, $\{\kappa_1, \kappa_2, \ldots, \kappa_n\}$, or the cortical thickness at each point, $\{t_1, t_2, \ldots, t_n\}$, are pointwise characteristics and should be primarily defined on the graph nodes rather than on edges. In accordance with an aspect of the present invention the exponential of the positive diagonal matrices $\exp(S)=\exp(\text{diag}(s_1, s_2, \ldots, s_n))$, and $\exp(K)=\exp(\text{diag}(\kappa_1, \kappa_2, \ldots, \kappa_n))$, and $\exp(T)=\exp(\text{diag}(t_1, t_2, \ldots, t_n))$ are used. In accordance with a further aspect of the present invention additional information is incorporated in the weighting of the nodes by defining the graph Laplacian as:

$$\tilde{L}=GL, \text{where } G=D^{-1}(c_s\exp(S)+c_\kappa\exp(K)+c_t\exp(T))^{-1}, \quad (2)$$

where $c_s$, $c_\kappa$ and $c_t$ and ct are weighting factors. For instance $c_s=\text{mean}\{D_{ii}\}_{i=1\ldots n}/\text{mean}\{\exp(s_i)\}_{i=1\ldots n}$ is used. The right eigenvectors of the Laplacian comprise the graph spectrum $\hat{X}=\{\hat{X}^{(1)}, \hat{X}^{(2)}, \ldots, \hat{X}^{(n)}\}$. FIG. 1 illustrates an example of spectral components for two brain hemispheres where each column depicts a different spectral component. Each eigenvector $\hat{X}^{(u)}$ represents a different (weighted) harmonic on a mesh surface that represents an intrinsic geometric property.

The values $\hat{x}^{(u)}$, i∈[1 . . . n], give the spectral coordinates for each point $x_i$. Eigenvectors associated with the lower non-zero eigenvalues (e.g., ($\hat{X}^{(2)}$, $\hat{X}^{(3)}$) represent coarse (low-frequency) intrinsic geometric properties of the shape, the first of them $\hat{X}^{(2)}$ is called the Fiedler vector, while eigenvectors associated with higher eigenvalues (e.g., $\hat{X}^{(n-1)}$, $\hat{X}^{(n)}$) represent fine (high-frequency) geometric properties. One idea of the method provided in accordance with an aspect of the present invention is to match two meshes X and Y by comparing their corresponding spectra $\hat{X}$ and $\hat{Y}$ rather than directly comparing the meshes themselves.

Ordering the Spectra

Each point of the brain surface mesh is represented with K spectral components associated with the K smallest eigenvalues, i.e., the embedded representations are $\hat{X}^K=[\hat{X}^{(2)}, \ldots, \hat{X}^{(K+1)}]$ and $\hat{Y}^K=[\hat{Y}^{(2)}, \ldots, \hat{Y}^{(K+1)}]$. Unfortunately, the spectral coordinates of the two meshes may not be directly comparable as a result of two phenomena. First, there exists a sign ambiguity when computing eigenvectors (i.e., if Ax=λx then A(−x)=λ(−x)), requiring a sign check of each eigenvector in the two meshes. Additionally, as a result of greater algebraic multiplicity of an eigenvalue, it may be possible that the ordering of the lowest eigenvectors will change, e.g., if two eigenvectors correspond to the same eigenvalue in both meshes, then the solver may compute these eigenvectors in one order for the first mesh and in the opposite order for the second mesh. For large meshes, this is a recurrent problem and the eigenvectors must be reordered. Since different brains do not present major discrepancies or major articulated deformations between individuals, the eigenvectors may be reordered by comparing their values at all pairs of closest points between the two brain hemispheres.

To speed up the reordering, all eigenvectors are first subsampled by selecting randomly a few points (500 points are used in experiments related to aspects of the present invention). Their spectral coordinates are normalized between 0 and 1 and denoted as $\hat{x}^{(i)}$. A spatial integration of all differences within pairs of closest points provides a similarity measure, i.e., if the eigenvectors $\hat{x}^{(i)}$ and $\hat{y}^{(j)}$ correspond to each other in both meshes, for all closest Cartesian points $\{(x_i, y_{i'})\}_{i=1 \ldots n}$, the difference of their associated spectral coordinates are computed. All the differences of potentially corresponding eigenvectors, $\hat{x}^{(u)}$ and $\hat{y}^{(v)}$, are gathered in a dissimilarity matrix, $C(\hat{x}^{(u)}, \hat{y}^{(v)})=\sum_{i=1}^{N}(\hat{x}_i^{(u)}-\hat{y}_{i'}^{(v)})^2$ where $y_{i'} \in Y$ is closest to $x_i \in X$. The Hungarian algorithm may be used to find an optimal permutation of eigenvectors $\hat{y}^{(v)}$ and, in order to remove the sign ambiguity, the minimal dissimilarity between the comparison of $\hat{x}^{(u)}$ and $\hat{y}^{(v)}$, and $\hat{x}^{(u)}$ and $-\hat{y}^{(v)}$ is used. The cost matrix used in the Hungarian algorithm is $Q(u, v)=\min\{C(\hat{x}^{(u)}, \hat{y}^{(v)}), C(\hat{x}^{(u)}, -\hat{y}^{(v)})\}$. After permutation, any eigenvector $\hat{x}^{(u)}$ corresponds with $\hat{y}^{(u)}$ and has a permutation cost $C^{(u)}$.

Alignment of Spectra

After reordering and handling the sign ambiguity, the eigenvectors of the two meshes may be assumed to have the same ordering in both embeddings (i.e., $\hat{x}^{(u)}$ corresponds with $\hat{y}^{(u)}$). However, the embedded representations, $\hat{X}^K$ and $\hat{Y}^K$, need to be aligned (as illustrated in the third panel 203 of FIG. 2 both spectra have slight differences) so that closest points in these embedded representations would reveal corresponding points in both shapes (i.e., if $\hat{y}_j^K$ is the closest point to $\hat{x}_i^K$, then $x_i$ corresponds with $y_j$).

In order to perform this alignment, each eigenvector $\hat{x}^{(u)}$ is first weighted with $\exp(-(C^{(u)}\lambda_{\hat{X}^{(u)}})^2/2\sigma^2)$, where $C^{(u)}$ is the permutation cost, $\lambda_{\hat{X}^{(u)}}$ is its associated eigenvalue, and σ is a penalizing factor, using $\sigma=\text{mean}\{C^{(u)}\lambda_{\hat{X}^{(u)}}\}_{u=1 \ldots K}$. Low-frequency eigenvectors, associated with coarser geometric properties (i.e., small eigenvalues $\lambda_{\hat{X}^{(u)}}$), will thus have more importance than the high-frequency eigenvectors associated with finer details, and pairs of corresponding eigenvectors will have more importance if they have strong similarities (i.e., low permutation costs $C^{(u)}$).

To further constrain the alignment of the mesh representations, extra information is added as additional coordinates to the embedded representation. Specifically, the first K spectral components $\hat{X}^K=[\hat{X}^{(2)}, \ldots, \hat{X}^{(K+1)}]$ are concatenated with the extra coordinates, exp(S), exp(K), and exp(T). These extra components are also normalized to be comparable with the spectral coordinates. The embedded representations to be aligned are thus:

$$\tilde{X}=[\hat{X}^K, c_s\exp(S_X), c_K\exp(K_X), c_t\exp(T_X)], \text{and},$$

$$\tilde{Y}=[\hat{Y}^K, c_s\exp(S_Y), c_K\exp(K_Y), c_t\exp(T_Y)]. \quad (3)$$

It is believed that providing extra feature based coordinates in addition to the spectral coordinates as shown in equation (3) is novel in spectral correspondence.

The alignment of the spectral components can be viewed as a nonrigid registration, $\tilde{X}^K=\Phi(\tilde{Y}^K)$. The third panel 203 of FIG. 2 shows the alignment challenge where the first three spectral components ($\hat{X}^{(2)}$, $\hat{X}^{(3)}$, $\hat{X}^{(4)}$) are used as 3D (x, y, z) coordinates for visualization purposes. The Robust Point Matching with a thin plate spline-based transformation is often used for 2D or 3D registration. However, with this approach, the final registration depends on the number and choice of the control points. The Coherent Point Drift method as described in "A. Myronenko and X. Song. Point-set registration: Coherent point drift. PAMI, 2009" was applied which is fast and demonstrates excellent performance in this application.

To increase speed in the present method which is provided as an aspect of the present invention, $\tilde{X}$ and $\tilde{Y}$ are subsampled by taking randomly a few points (500 points were used). The Coherent Point Drift method finds a continuous transformation Φ that can be applied on all points of $\tilde{Y}$. After aligning both embedded representations (i.e., $\tilde{X}=\Phi(\tilde{Y})$), it is possible to directly compare them, i.e. two points which are closest in the embedded representations, $\tilde{x}_i$ and $\tilde{y}_{i'}$, are treated as corresponding points in the meshes X and Y. The fourth panel 204 of FIG. 2 illustrates a few pairs of corresponding points. All pairs of points connected by the red lines have the closest embedded coordinates.

Results

The methodology as provided in accordance with an aspect of the present invention introduces several new concepts for spectral methods and shows how these methods may be customized for the application of cerebral cortex matching. It will be first shown in an intuitive experiment the effect of node weighting on a simple mesh. Second, the accuracy of spectral methods will be measured on a controlled experiment with a known ground truth. Third, the accuracy will be analyzed of the method provided herein as an aspect of the present invention against FreeSurfer. For this comparison 24 cerebral hemispheres were used from 12 subjects, and the comparison was based on 288 matches using different combinations of additional information. Each brain surface mesh has been extracted using FreeSurfer from $T_1$-weighted magnetic resonance images.

Node Weighting

It is believed that methods provided herein as an aspect of the present invention are the first to utilize node weights in a spectral correspondence approach. Consequently, some space is briefly devoted to give an intuition about the behavior of these node weights in the context of spectral correspondence. To demonstrate the differences in weighting the edges and the nodes, the Fiedler vector is shown on a spherical mesh with an asymmetric vertex distribution. The concentration of vertices at the poles guides the spectral eigendecomposition (i.e., the Fiedler vector is aligned with the sphere poles as shown in top-left sphere of FIG. 3). The accumulation of Fiedler vector on randomly orientated spheres should yield a uniform distribution (as shown in the bottom-left sphere of FIG. 3). Encoding weights on nodes can influence the orientation of the Fiedler vector. For instance, to reorient the Fiedler vector vertically, a texture data is used where the top section and the bottom sections of a sphere (on a world z axis) are heavily weighted. For all points $\{x_i\}_{i=1,\ldots,n}$, their weights are $\Theta=[\theta_1, \theta_2, \ldots, \theta_n]$ where $\theta_i=1000$ if $|x_i^{(z)}|\geq 0.4$ (i.e., a large weighting at the top and bottom of the sphere along the z axis) and $\theta_i=1$ if $|x_i^{(z)}|\leq 0.4$ (i.e., a low weighting around the middle section).

Figure 3:
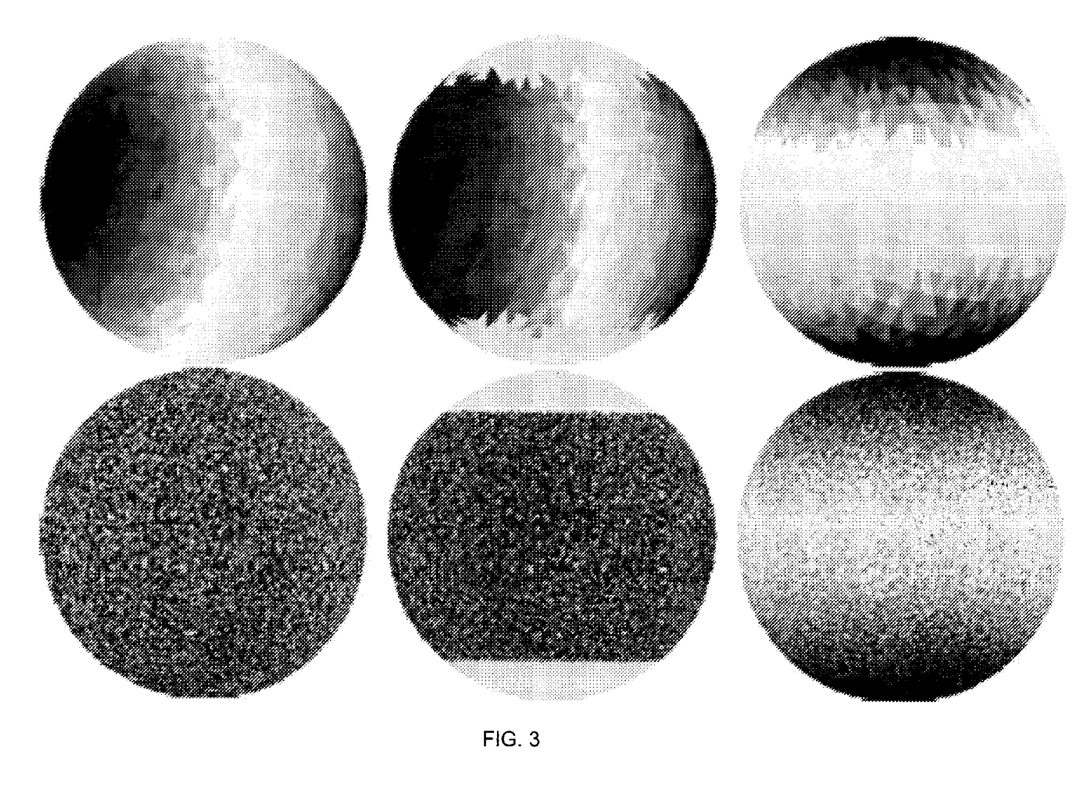
FIG. 3 illustrates node weighting in a graph in accordance with another aspect of the present invention.

Accordingly, FIG. 3 illustrates the effect of node weighting. In FIG. 3, the Top Row, three cases showing the Fiedler vector on spheres of same orientation, wherein: left, with no weighting: the vector is aligned with the sphere axis; middle, with edge weighting: the top and bottom sections of the sphere are masked; right, with node weighting: the vector is reorientated vertically. Bottom Row: Same three experiments ran on 100 randomly orientated spheres. Their Fiedler vectors are accumulated. The reorientation of the Fiedler vector via node weighting (bottom-left) is clearer.

In previous approaches to spectral correspondence, weights are encoded on graph edges. The texture weight $\Theta$ is added to the edge weights as provided in equation (1): $w_{ij}=(\text{dist}(x_i,x_j)+\epsilon)^{-1}\times(|\theta_i-\theta_j|+\epsilon)^{-1}$. The resulting weighting will highlight the texture boundaries isolating three distinct regions: the top, the middle, and the bottom section. This creates a multiplicity of three in the zero eigenvalues, and as shown in the top-middle sphere of FIG. 3, the Fiedler vector covers the largest section.

In the method provided as an aspect of the present invention, nodes are weighted in a graph in addition to weighting the edges. In order to compare with the previous experiment, the texture $\Theta$ is not incorporated on graph edges. It is now used on graph nodes as provided by equation (2) $G=D^{-1} \text{diag}(\Theta)^{-1}$. After the spectral decomposition, the multiplicity of the zero eigenvalue is 1 (i.e., there is one distinct object), and the Fiedler vector is aligned with the texture (i.e., with the world z axis). To verify this alignment, this experiment was repeated with 100 spheres orientated randomly and the values of the Fiedler vectors were accumulated (bottom row of FIG. 3). The principal axis of the accumulated values, (−0.04, 0.12, 0.99), is indeed vertical when weighting the graph nodes (bottom-right of FIG. 3). The accumulation of the Fiedler vectors does not show an apparent principal axis when weighting only the graph edges (bottom-middle of FIG. 3), or when the texture data is not used (bottom-left of FIG. 3).

These three experiments show that weighting the graph nodes provides a new way for incorporating additional pointwise information and behaves differently than weighting the graph edges. Spectral methods can thus benefit from this idea, not only in cortex matching, but in various applications. The next experiment shows how node weighting improves matching in spectral methods.

Matching Deformed Brain Surfaces

Figure 4:
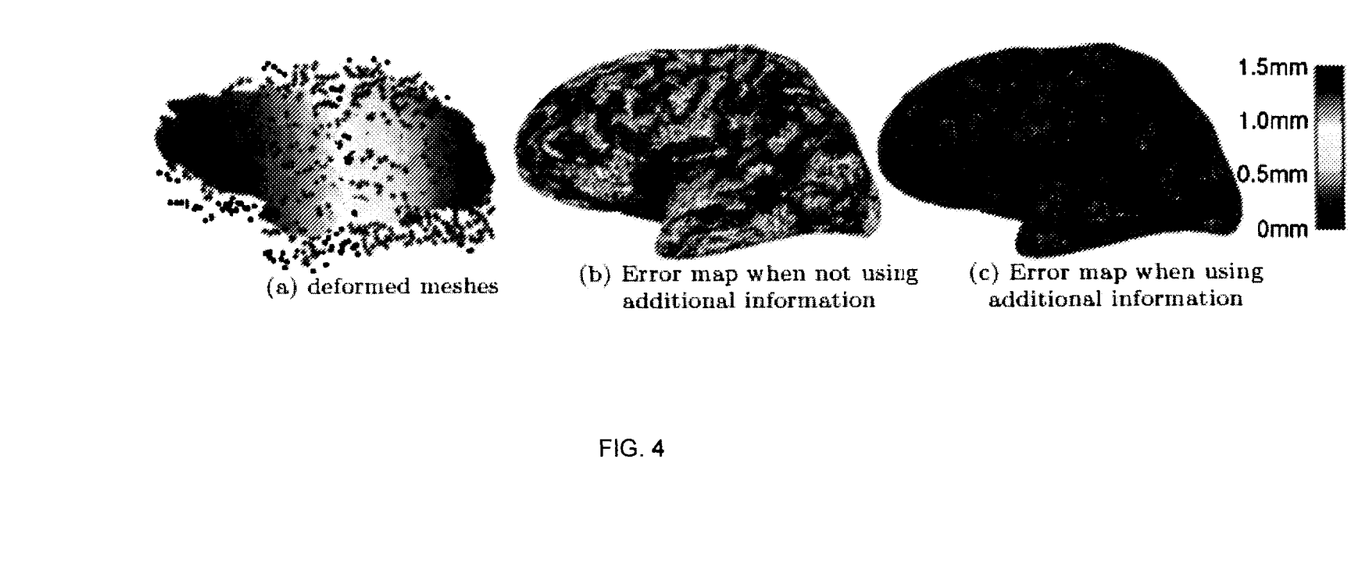
FIG. 4 illustrates an aspect of spectral correspondence in accordance with an aspect of the present invention in relation to a ground truth.

Every individual has a unique folding pattern in the cerebral cortex, however there are many large-scale similarities. Before considering inter-subject cortex matching, the intra-subject case will be studied. This will be done with a controlled, simulated deformation to analyze how additional information improves the accuracy of the method as an aspect of the present invention, and how the additional information should be incorporated. For the experiment, one brain hemisphere will be matched with a deformed version of itself. The vertex indexing remains the same in the deformed version, therefore the true matching is known (i.e., for all i, vertex $p_i$ in the first mesh should match the vertex $q_i$ in the second mesh). One of the cortical hemisphere surface models is severely deformed with the transformation $q^{(z)}=(1+\alpha)p^{(z)}$ (a compression in the z-axis controlled by $\alpha$) and $q^{(x)}=p^{(x)}+\beta r^2/\max(r^2)$ with $r^2=p^{(x)^2}+p^{(y)^2}$ (a radial distortion controlled by $\beta$). This simulates a deformation due to a drastic change in the head shape. The deformation, however, preserves the same mesh topology (i.e., with no discontinuity and no intersecting faces). FIG. 4 illustrates the position of the original hemisphere with the dots and the deformed hemisphere with the mesh. The accuracy of the matching in accordance with an aspect of the present invention is quantified by measuring the mean distance between all points and their corresponding matched points. That is, for all points $p_i$ in mesh 1 matching $q_j$ in mesh 2, the distance: $\text{mean}(\text{dist}(p_i, p_j))$ is averaged. When no additional information is used, as it is the case in most state-of-the-art spectral methods, an average error distance of 0.44 mm is found as shown in the first error map of FIG. 4. Most errors are actually located on the sulci extrema.

Additional information can be incorporated as node weighting by using equation (2); as edge weighting by similarly adding additional term to equation (1) such as $w_{ij}=1/(d(i,j)+\epsilon)\exp(-(s_i-s_j)^2/2\sigma_s^2)\exp(-(\kappa_i-\kappa_j)^2/2\sigma_\kappa^2)\exp(-(t_i-t_j)^2/2\sigma_t^2)$, where $\sigma_{s,\kappa,t}$ are penalizing factors; or as additional coordinates in the alignment process by using equation (3). Three sources of additional information (sulcal depth, surface curvature, and cortical thickness) can thus be used in three different ways in the method provided in accordance with an aspect of the present invention. That is 512 possible combinations ($2^{3\times 3}$) which were all applied and it was found that adding information as additional coordinate has the strongest impact on the accuracy of the matching. Adding the sulcal depth as the only additional feature yields an error of 0.16 mm; adding only the surface curvature yields an error of 0.35 mm; and the cortical thickness yields an error of 0.14 mm. Adding single or multiple source of additional information on only the graph nodes does not yield significant improvement (0.44 mm), nor does representing this additional information on only the graph edges (0.44 mm). However, by adding all three features and using all of them on the graph nodes and on the graph edges, the error drops to 0.06 mm. The best combination of additional information was obtained when using all three features and when using sulcal depth and cortical thickness on the graph nodes, yielding an error of 0.05 mm. The error map in the right of FIG. 4 shows an almost perfect matching with the best-performing combination.

In summary on FIG. 4, this figure illustrates a comparison with ground truth. Left FIG. 4(a): The deformed mesh (with its Fiedler vector) overlaid with the original vertex positions illustrated by the dots. Middle FIG. 4(b): The mean distance error is 0.44 mm with a standard spectral correspondence method (i.e., without additional information). Right FIG. 4(c): With additional information (sulcal depth, surface curvature, and cortical thickness), the error drops to 0.05 mm.

Validation

Brain surface matching is an ambiguous problem. Indeed, sulci morphology and topology differ from one individual to another. There is no ground truth available for perfect brain surface matching. However, FreeSurfer as described in "B. Fischl, M. I. Sereno, R. B. Tootell, and A. M. Dale. High-resolution intersubject averaging and a coordinate system for the cortical surface. Human Brain Mapping, 8(4), 1999" has been demonstrated to provide highly accurate cortical matchings that closely align cortical areas across subjects as described in "O. P. Hinds, N. Rajendran, J. R. Polimeni, J. C. Augustinack, G. Wiggins, L. L. Wald, Diana H. Rosas, A. Potthast, E. L. Schwartz, and B. Fischl. Accurate prediction of V1 location from cortical folds in a surface coordinate system. NeuroImage, 39(4), 2008" and therefore provides a reliable benchmark for our comparison. The delineations of 81 sulcal regions are available for 24 hemispheres (12 subjects). These sulcal regions were obtained using an automatic parcellation of the cortex as described in "B. Fischl, A. van der Kouwe, C. Destrieux, E. Halgren, F. Segonne, D. H. Salat, E. Busa, L. J. Seidman, J. Goldstein, D. Kennedy, V. Caviness, N. Makris, B. Rosen, and A. M. Dale. Automatically parcellating the human cerebral cortex. Cereb. Cortex, 14(1), 2004" and are considered as a standard herein.

Figure 5:
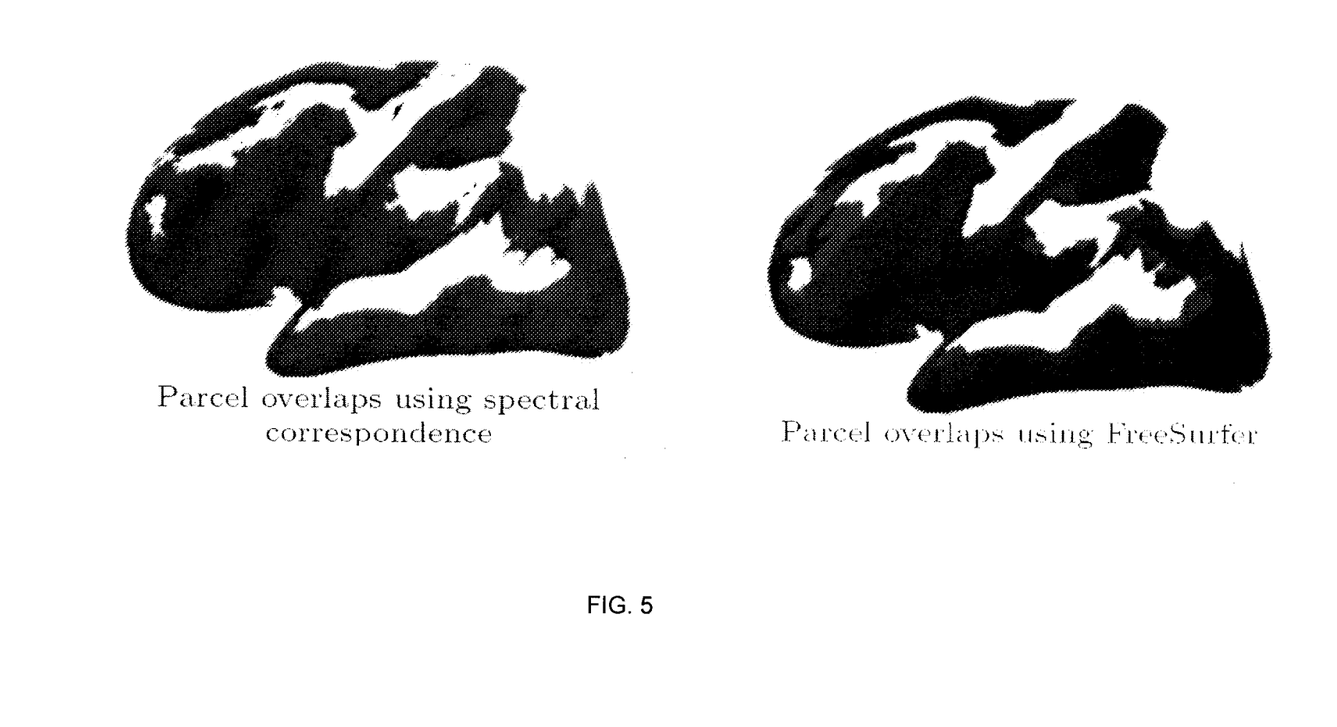
FIG. 5 illustrates a comparison of parcel overlaps in a brain wherein a correspondence was determined in accordance with an aspect of the present invention.

Although folding parcellations are not accepted to align between subjects in all cases (except for the primary folds), they do provide means to compare the two methods. Correspondence maps generated by FreeSurfer and by the method provided as an aspect of the present invention are used to project the parcellation areas onto different brain hemispheres and their overlaps are measured (illustrated in FIG. 5) and shows the areas where the projected sulcal regions of two cortices overlap, and where the projection mismatches. (Left brain) Correspondences were computed in 124 seconds using our method, while (right brain) FreeSurfer required several hours.

To process a mesh of 135,000 vertices, FreeSurfer has a varying processing time which is always on the order of several hours, while the time required by the method provided as an aspect of the present invention is just on the order of a few minutes. To process all 288 possible pairs of left and right brain hemispheres, the method provided in accordance with an aspect of the present invention required on average 124 seconds on a 2.8 GHz Intel Pentium 4 using unoptimized Matlab code (with meshes of 20,000 vertices, this method performed in 19 seconds). The code could benefit further from parallel programming and the use of GPU. The total time for processing all possible pairs was 9 hours on a single computer, a substantial advantage compared to the several weeks required by FreeSurfer to process all 288 cortex matchings in series. Each overlap ratio is defined by the ratio of set intersection to set union.

Figure 6:
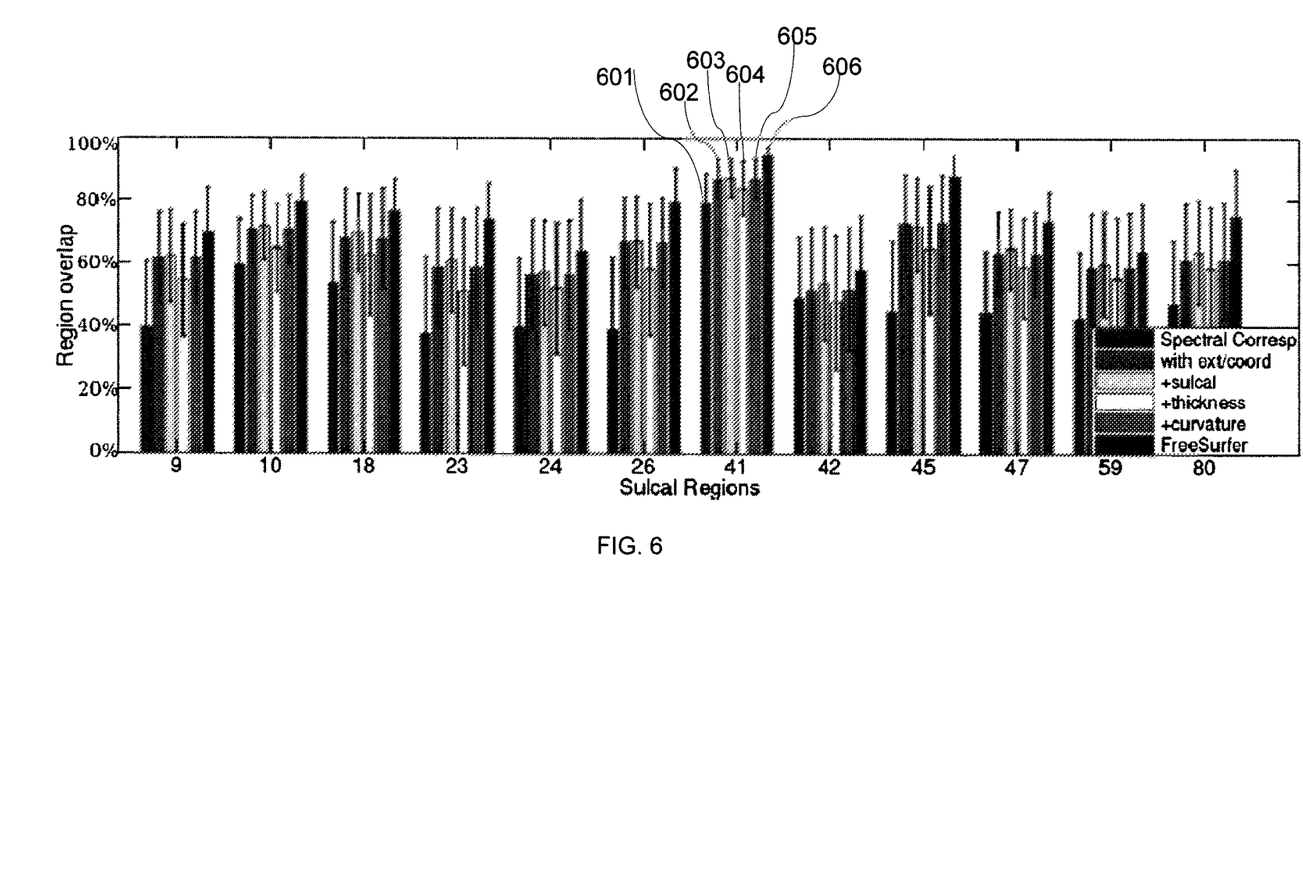
FIG. 6 illustrates a comparison of the method provided in accordance with an aspect of the present invention with a known method.

FIG. 6 shows the overlap ratios for the largest sulcal parcellations using the method provided in accordance with an aspect of the present invention compared with Freesurfer. The results are shown in numbered groups of 6 bars, which represents a sulcal region. Of one group (sulcal region 41) the detailed bars are identified: 601 is the bar indicating spectral correspondence, 602 with extended coordinates, 603 with sulcal depth, 604 with thickness, and 605 with curvature feature added to weighting and/or coordinates as explained above. Bar 606 shows the results of Freesurfer. All bar groups representing a sulcal region are ordered in a similar way. Overlap ratios are shown of different sulcal regions in several settings. With no additional information (601) 65% of FreeSurfer's performance was achieved; with all additional information (sulcal depth, cortical thickness and cortical curvature) as extra coordinates (602) 87% of Freesurfer was achieved; with all additional information as extra coordinates and sulcal depth on graph nodes and graph edges (603) 88% of Freesurfer was achieved; with all additional information as extra coordinates and cortical thickness on graph nodes and graph edges (604) 78% of Freesurfer was achieved; with all additional information as extra coordinates and cortical curvature on graph nodes and graph edges (605) 87% of Freesurfer was achieved; and 606 indicates results by FreeSurfer (requiring weeks of computations). The method provided in accordance with an aspect of the present invention only requires 9 hours and is strongly correlated with FreeSurfer (correlation coefficient of $\rho$=0.816). The error bars in FIG. 6 show the standard deviation of each overlap ratio. The results are consistent across all 81 sulcal regions (i.e., whenever FreeSurfer outputs a higher overlap ratio, the herein provided method also consistently outputs a higher overlap ratio). Specifically, the results are correlated to FreeSurfer's overlaps with a correlation coefficient of $\rho$=0.816.

The sulcal regions as numbered in FIG. 6 have the meaning: 9 (G frontal middle), (G frontal middle), 18 (G occipit temp med Lingual part), 23 (G parietal inferior Supramarginal part), 24 (G parietal superior), 26 (G precentral), 41 (Medial wall), 42 (Pole occipital), 45 (S central), 47 (S cingulate Main part and Intracingulate), 59 (S intraparietal and Parietal transverse), and 80 (S temporal superior).

When comparing larger regions (illustrated in FIG. 6: parcels 9, 10, 18, 23, 24, 26, 41, 42, 45, 47, 59, and 80, as defined in "B. Fischl, A. van der Kouwe, C. Destrieux, E. Halgren, F. Segonne, D. H. Salat, E. Busa, L. J. Seidman, J. Goldstein, D. Kennedy, V. Caviness, N. Makris, B. Rosen, and A. M. Dale. Automatically parcellating the human cerebral cortex. Cereb. Cortex, 14(1), 2004), FreeSurfer's overlap ratios are on average 74%. In its best setting (using sulcal depth as additional information), the herein provided method for these specific settings can provide 88% that of FreeSurfer's overlap ratios.

Combination of Additional Information

Besides information on sulcal depth, access was available to information on cortical thickness and on surface curvature. The cortical thickness is another clinically relevant anatomical measure, which is calculated by FreeSurfer from anatomical MRI images. The sulcal curvature is estimated with the Gaussian curvature ($\kappa_1 \kappa_2$) of the mesh. The performance of the method provided in accordance with an aspect of the present invention was first analyzed using five configurations of different combinations of additional features. For each configuration, the method provided in accordance with an aspect of the present invention was performed on the 288 pairs of brain hemispheres (totaling 1440 matchings). The results are summarized in FIG. 6.

The first configuration uses no additional information ($G=D^{-1}$ in equation (2)). In that configuration, the average overlap ratio on the largest parcels is only 48% (in comparison, FreeSurfer performs at 74%). In the second configuration, sulcal depth, cortical thickness, and cortical curvature are used as extra coordinates in the spectral alignment (using equation (3)). The average overlap ratio increases to 64% (or 87% of FreeSurfer's performance), a 34% increase from the previous configuration. As shown in the previous experiments, using additional information as extra coordinates does increases the accuracy. In the third configuration, also all additional information as extra coordinates is used, and sulcal depth information is added on graph nodes ($G=D^{-1} \exp(S)^{-1}$ in equation (2)) and on graph edges (in equation (1), $w_{ij}=1/(d(i,j)+\epsilon)\exp(-(s_i-s_j)^2/2\sigma_s^2)$ where $\sigma_s$ is a regularization term). This configuration is actually the best one in which the method performed. The average overlap ratio is 66% (or 88% of FreeSurfer's performance). This suggests that sulcal depth provides crucial information when matching brain hemispheres, as has been previously suggested by "B. Fischl, M. I. Serena, R. B. Tootell, and A. M. Dale. High-resolution inter-subject averaging and a coordinate system for the cortical surface. Human Brain Mapping, 8(4), 1999."

The fourth configuration adds cortical thickness as additional information on graph nodes ($G=D^{-1}\exp(T)^{-1}$ in equation (2)) and on graph edges (in equation (1), $w_{ij}=1(d(i,j)+\epsilon)\exp(-(t_i-t_j)^2/2\sigma_t^2)$). Using cortical thickness alone actually worsen the overlap ratio to 58% (or 78% of FreeSurfer's performance). This suggests that cortical thickness may be a contradictory information in the spectral correspondence method. The fifth configuration uses cortical curvature as additional information on graph nodes ($G=D^{-1}\exp(K)^{-1}$ in equation (2)) and on graph edges (in equation (1), $w_{ij}=1/(d(i,j)+\epsilon)\exp(-(\kappa_i-\kappa_j)^2/2\sigma_\kappa^2)$). Cortical curvature shows to be also a significant additional information as it increases the average overlap ratio to 64% (or 87% of FreeSurfer's performance).

It is noted that there is no perfect configuration of additional information. The experiments showed that certain configurations perform better on particular parcellations rather than on others. The right configuration of additional information thus depends on which sulcal region of the brain should be matched. That said, the experiments suggest that sulcal depth and cortical curvature are significant additional information that improve the matching method as provided herein.

In summary, cerebral cortex matching is an important topic that facilitates basic computational study in neuroscience. Current, surface-based matching methods can be quite accurate, but very slow. A new cortex matching method based on spectral correspondence operating at speeds of several orders of magnitude faster than current methods is provided herein. Furthermore, spectral methods are extended in order to use additional information as weights in graph nodes and as extra embedded coordinates with little or no computational expense. This added flexibility makes the herein provided spectral correspondence method a good candidate for brain studies involving many additional information. The current best configuration of additional information were found when using sulcal depth, surface curvature, and cortical thickness, as extra embedded coordinates and sulcal depth on graph nodes and graph edges. The herein provided brain surface matching method far outperforms the accuracy of the more commonly used volumetric methods and approaches FreeSurfer's level of accuracy when aligning sulcal regions (88% of FreeSurfer's performance). The vast increase in speed and the added exibility when using additional information gives new perspectives to previously computationally prohibitive experiments. The contribution new features incorporated to help improve the matching (e.g., anatomical or functional features extracted from various data sources) can be tested. Quick parameter sweeps can be performed to isolate the best parameter value sets. These computationally intensive experiments can help to understand what features are consistently correlated with brain areas across individuals and what their role are during the development of the cortical folding pattern. Currently, the correspondences found with the pairs of closest spectral neighbors. New schemes, such as the Relaxation Labeling as proposed in "Y. Zheng and D. Doermann. Robust point matching for nonrigid shapes by preserving local neighborhood structures. PAMI, 28(4), April 2006" may improve accuracy.

Figure 7:
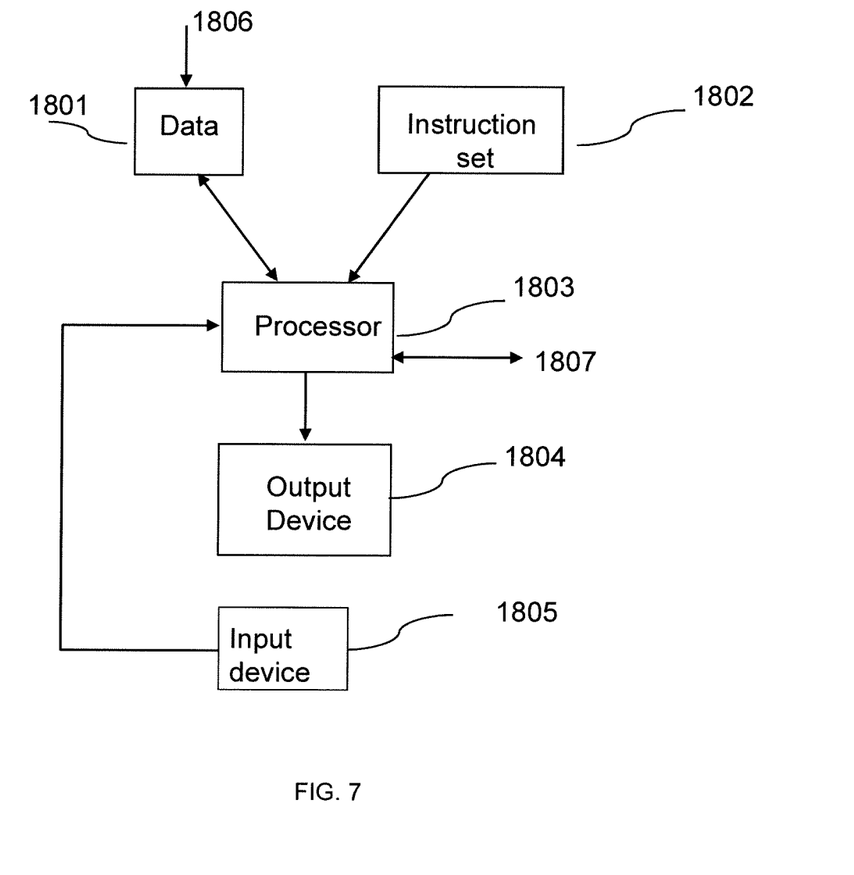
FIG. 7 illustrates a system in accordance with an aspect of the present invention.

The methods as provided herein are, in one embodiment of the present invention, implemented on a system or a computer device. A system illustrated in FIG. 7 and as provided herein is enabled for receiving, processing and generating data. The system is provided with data that can be stored on a memory 1801. Data may be obtained from a scanning machine such as an MRI (Magnetic Resonance Imaging) machine or may be provided from a data source. Data may be provided on an input 1806. The processor is also provided or programmed with an instruction set or program executing the methods of the present invention that is stored on a memory 1802 and is provided to the processor 1803, which executes the instructions of 1802 to process the data from 1801. Data, such as a matching or correspondence map or any other signal resulting from the processor can be outputted on an output device 1804, which may be a display to display data or a loudspeaker to provide an acoustic signal. The processor also has a communication channel 1807 to receive external data from a communication device and to transmit data to an external device. The system in one embodiment of the present invention has an input device 1805, which may be a keyboard, a mouse or any other device that can generated data to be provided to processor 1803. The processor can be dedicated hardware. However, the processor can also be a CPU or any other computing device that can execute the instructions of 1802. Accordingly, the system as illustrated in FIG. 7 provides a system for data processing resulting from an imaging device or any other data source and is enabled to execute the steps of the methods as provided herein as an aspect of the present invention.

Other Applications of Spectral Correspondence

The herein provided methods of spectral correspondence with inclusion of external features in spectral or graph representations as either node weights or as coordinates of the spectral elements that are being compared are illustrated by comparing cortical surfaces. The herein provided methods are not limited to comparing data representing cortical surfaces, but can be applied to any comparison of sets of data to produce a correspondence between elements of the sets of data, wherein a set of data can be represented in a graph where upon the comparative methods as provided herein can be applied. For instance, a set of data may represent a network such as a social network of members that operates on the Internet or under the World Wide Web and wherein a member has certain features. In another example a set of data may represent an electrical network, wherein a member (such as a passive electrical element) has certain features. In yet another example a set of data may represent an image, wherein a pixel has certain features.

Increasingly large datasets are being collected to describe complex systems. These systems operate at the micro scale (chemical and biological systems), the macro scale (social interactions) and the mega scale (distribution, transportation and communication). Relationships between the elements of these systems can be considered as a network (graph). Aspects of the present invention can be used to provide a correspondence between the elements of two networks that seeks to preserve local and global relationships of the elements to each other and the system while also preserving identifying features of the elements. In one example provided herein of brain surface matching, the elements are points on the surface, the relationships are defined by the local surface connectivity and example features are defined by the sulcal depth or surface curvature. These features, such as sulcal depth, in accordance with an aspect of the present invention are quantified and each node in a graph is associated with a relevant value of the feature.

Objects like a brain or data representing complex structure have many features that can be quantified. In accordance with an aspect of the present invention a data element in a set of data representing the complex structure can be associated with one or more features, wherein each feature has a value. In the case of providing a correspondence between two electrical networks, the elements could be electrical terminals or junctions, the relationships could be defined by electrical connections, and the features could be desired power consumption or material composition. Which features are selected and how they are obtained depends on the application. As was described earlier methods for obtaining brain features, such as sulcal depth, brain curvature, and cortical thickness are well known. To incorporate these features in coordinates of a node in a graph and in a weight of a node are believed to be novel aspects of the present invention. In the case of providing a correspondence between two social networks, the elements could be people, the relationships could be social relationships and the features could be descriptions of position, skills or the number of friends.

The following references are generally descriptive of the background of the present invention and are hereby incorporated herein by reference: [1]. K. Amunts, A. Malikovic, H. Mohlberg, T. Schormann, and K. Zilles. Brodmann's areas 17 and 18 brought into stereotaxic space-where and how variable? NeuroImage, 11(1), 2000. [2]. Q. Anqi, D. Bitouk, and M. I. Miller. Smooth functional and structural maps on the neocortex via orthonormal bases of the Laplace-Beltrami operator. Trans. Med. Im., 25(10), 2006. [3]. F. Chung. Spectral Graph Theory (CBMS Conf. in Math., No. 92). AMS, 1997. [4]. H. A. Drury, D. C. Van Essen, S. C. Joshi, and M. I. Miller. Analysis and comparison of areal partitioning schemes using 2-D uid deformations. NeuroImage, 3, 1996. [5]. B. Fischl, N. Rajendran, E. Busa, J. Augustinack, O. Hinds, B. T. Thomas Yeo, H. Mohlberg, K. Amunts, and K. Zilles. Cortical folding patterns and predicting cytoarchitecture. Cereb Cortex, 18(8), 2007. [6]. B. Fischl, M. I. Sereno, R. B. Tootell, and A. M. Dale. High-resolution intersubject averaging and a coordinate system for the cortical surface. Human Brain Mapping, 8(4), 1999. [7]. B. Fischl, A. van der Kouwe, C. Destrieux, E. Halgren, F. Segonne, D. H. Salat, E. Busa, L. J. Seidman, J. Goldstein, D. Kennedy, V. Caviness, N. Makris, B. Rosen, and A. M. Dale. Automatically parcellating the human cerebral cortex. Cereb. Cortex, 14(1), 2004. [8]. L. Grady and J. R. Polimeni. Discrete Calculus: Applied Analysis on Graphs for Computational Science. Springer, 2010. [9]. O. P. Hinds, N. Rajendran, J. R. Polimeni, J. C. Augustinack, G. Wiggins, L. L. Wald, Diana H. Rosas, A. Potthast, E. L. Schwartz, and B. Fischl. Accurate prediction of V1 location from cortical folds in a surface coordinate system. NeuroImage, 39(4), 2008. [10]. V. Jain and H. Zhang. Robust 3D shape correspondence in the spectral domain. In Int. Conf. on Shape Mod. and App., 2006. [11]. G. Lohmann, D. Y. von Cramon, and A. C. Colchester. Deep sulcal landmarks provide an organizing framework for human cortical folding. Cereb Cortex, 18(6), 2008. [12]. D. Mateus, R. Horaud, D. Knossow, F. Cuzzolin, and E. Boyer. Articulated shape matching using Laplacian eigenfunctions and unsupervised point registration. In CVPR, 2008. [13]. A. Myronenko and X. Song. Point-set registration: Coherent point drift. PAMI, 2009. [14]. M. Niethammer, M. Reuter, F. E. Wolter, S. Bouix, N. Peinecke, M. S. Koo, and M. Shenton. Global Medical Shape Analysis Using the Laplace-Beltrami Spectrum. In MICCAI, 2007. [15]. M. Reuter. Hierarchical shape segmentation and registration via topological features of Laplace-Beltrami eigenfunctions. Int. Journal Comp. Vis., 2009. [16]. M. Reuter, F. E. Wolter, M. Shenton, and M. Niethammer. Laplace-Beltrami eigenvalues and topological features of eigenfunctions for statistical shape analysis. Comput. Aided Des., 41(10), 2009. [17]. G. L. Scott and H. C. Longuet-Higgins. An algorithm for associating the features of two images. Proc Bio. Sc., 244(1309), 1991. [18]. L. S. Shapiro and J. M. Brady. Feature-based correspondence: an eigenvector approach. Image Vis. Comp., 10(5), 1992. [19]. J. Talairach, G. Szikla, P. Tournoux, A. Prosalentis, M. Bordas-Ferrier, L. Covello, M. Iacob, and E. Mempel. Atlas d'anatomie stereotaxique du telencephale. Masson, Paris, 1967. [20]. P. Thompson and A. W. Toga. A surface-based technique for warping three-dimensional images of the brain. Trans. on Med. Im., 15(4). 1996. [21]. S. Umeyama. An eigendecomposition approach to weighted graph matching problems. PAMI, 10(5), 1988. [22]. D. C. Van Essen and H. A. Drury. Structural and functional analyses of human cerebral cortex using a surface-based atlas. J. Neurosci., 17(18), 1997. [23]. Y. Zheng and D. Doermann. Robust point matching for nonrigid shapes by preserving local neighborhood structures. PAMI, 28(4), April 2006.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method for determining a correspondence between a first set of data and a second set of data, representing a first brain and a second brain, respectively, comprising:
   a processor creating a first mesh from the first set of data and a second mesh from the second set of data;
   the processor determining a Laplacian matrix for a weighted graph representing a mesh;
   determining by eigendecomposition a first and a second spectrum related to the first and second mesh;
   assigning to each node in each mesh a coordinate based on one or more spectral components of the related spectrum;
   assigning to each node in each mesh an additional coordinate based on a quantified feature of the node;
   aligning the reordered first and second spectrum to determine a correspondence between the first and second mesh.

2. The method of claim 1, wherein the Laplacian matrix reflects a weight of a node in its related weighted graph that expresses a quantified feature of the node.

3. The method of claim 2, wherein the quantified feature is selected from the group consisting of a sulcal depth, a brain curvature and a cortical thickness.

4. The method of claim 2, wherein weighting of nodes in the Laplacian matrix is achieved by evaluating an expression:

$$\tilde{L} = GL, \text{with}$$

$\tilde{L}$ representing the Laplacian matrix modified for node weights, L representing a Laplacian matrix that is unmodified for node weights and G representing a matrix of node weights.

5. The method of claim 4, wherein the matrix represented by G is dependent on at least one set of weighting factors of nodes, each weighting factor in the set being dependent on a quantified feature of that node.

6. The method of claim 1, wherein the quantified feature of the additional coordinate is selected from the group consisting of a sulcal depth, a brain curvature and a cortical thickness.

7. A system to determine a correspondence between a first set of data and a second set of data, representing a first brain and a second brain, respectively, comprising:
   a memory, enabled to store the first set of data, the second set of data and instructions;
   a processor, enabled to retrieve instructions from the memory to perform the steps:

creating a first mesh from the first set of data and a second mesh from the second set of data;

determining a first and a second Laplacian matrix for a weighted graph of the first and the second mesh, respectively;

determining by eigendecomposition a first and a second spectrum related to the first and second mesh;

assigning to each node in each mesh a coordinate based on one or more spectral components of the related spectrum;

assigning to each node in each mesh an additional coordinate based on a quantified feature of the node; and aligning the first and second spectrum to determine a correspondence between the first and second mesh.

8. The system of claim 7, wherein the first and second Laplacian matrix each reflects a weight of a node in its related weighted graph that expresses a quantified feature of the node.

9. The system of claim 8, wherein the quantified feature is selected from the group consisting of a sulcal depth, a brain curvature and a cortical thickness.

10. The system of claim 8, wherein weighting of nodes in the Laplacian matrix is achieved by evaluating an expression:

$\tilde{L}=GL$, with $\tilde{L}$ representing the Laplacian matrix modified for node weights, L representing a Laplacian matrix that is unmodified for node weights and G representing a matrix of node weights.

11. The system of claim 10, wherein the matrix represented by G is dependent on at least one set of weighting factors of nodes, each weighting factor in the set being dependent on a quantified feature of that node.

12. The system of claim 7, wherein the quantified feature of the additional coordinate is selected from the group consisting of a sulcal depth, a brain curvature and a cortical thickness.

* * * * *